United States Patent [19]
Isaac

[11] Patent Number: 5,915,392
[45] Date of Patent: Jun. 29, 1999

[54] TOOTHPICK CONTAINING DENTAL FLOSS

[76] Inventor: Amos Isaac, 139-34 231st St., Laurelton, N.Y. 11413

[21] Appl. No.: 09/098,613
[22] Filed: Jun. 17, 1998
[51] Int. Cl.⁶ .................................................. A61C 15/02
[52] U.S. Cl. ........................... 132/200; 132/321; 132/329
[58] Field of Search ..................................... 132/321, 200, 132/323, 324, 329; D28/65, 66, 68; 206/63.3, 63.5

[56] References Cited

U.S. PATENT DOCUMENTS

| | | | |
|---|---|---|---|
| 407,362 | 7/1889 | Mason | 132/321 |
| 2,856,938 | 10/1958 | Fleming | 132/323 |
| 3,744,499 | 7/1973 | Wells . | |
| 4,040,433 | 8/1977 | Edison . | |
| 4,304,245 | 12/1981 | Lichfield | 132/321 |
| 4,403,625 | 9/1983 | Sanders et al. | 132/323 |
| 4,836,227 | 6/1989 | Charaton . | |
| 4,852,728 | 8/1989 | Court | 132/321 |
| 5,174,314 | 12/1992 | Charaton . | |
| 5,224,501 | 7/1993 | McKenzie . | |

Primary Examiner—Todd E. Manahan
Assistant Examiner—Eduardo C. Robert
Attorney, Agent, or Firm—Michael I. Kroll

[57] ABSTRACT

The toothpick apparatus of the present invention consists of an elongated cylindrical device 13 having a thicker middle portion 17 tapering away from the middle toward opposing ends or points 19. The toothpick has a perforated area or break point near its middle 17 whereby when the toothpick is broken a useable length of dental floss 23 is exposed. The dental floss 23 is contained within layers of thin wood 21 which are rolled in order to form the toothpick. Additional embodiments of the present invention are also described.

1 Claim, 8 Drawing Sheets

TOOTHPICK CONTAINING DENTAL FLOSS

BACKGROUND OF THE INVENTION

1. Field of the Invention

The present invention relates generally to toothpicks and, more specifically, to a toothpick which is rolled from a flat piece of wood or formed from plastic and having located longitudinally along its center an amount of dental floss which is accessible when the toothpick is broken and the two pieces are pulled apart.

2. Description of the Prior Art

There are numerous toothpicks designed to remove food particles from between teeth. While these toothpicks may be suitable for the purposes for which they were designed, they would not be as suitable for the purposes of the present invention as heretofore described. It is thus desirable to provide a toothpick that contains an amount of dental floss within the frame of the toothpick.

Dental disease is caused by the accumulation of microscopic germs (bacteria) on the teeth and gums. These germs, which are always present even in healthy mouths, mix with saliva to form a transparent, sticky coating called bacterial plaque. Bacterial plaque generates acid which attacks the teeth, generally in the tiny crevices near the gum line between the teeth and the gum, resulting in tooth decay, tender and bleeding gums, foul breath, etc. The presence of bacteria alone in a disorganized state produces no harmful effects. To disorganize the bacteria daily will greatly reduce, if not eliminate, dental disease.

Dental floss, has been used to break up colonies of bacteria that gather at or near the gum line of the teeth. However, dental floss used haphazardly is not enough to completely disorganize the bacterial colonies found near the gum lines in all mouths since the gum line is not always penetrated by improper flossing.

McKENZIE, CLANCY D.

TOOTH-FLOSSING DEVICE

U.S. Pat. No. 5,224,501

A device for holding and manipulating dental floss for the removal of food particles, tartar and plaque from the teeth is described in which a loop of dental floss is connected between a pair of separate handles; the loop of dental floss being long enough to permit lateral motion across the tooth surface. The devices are either disposable or sterilizable for reuse.

WELLS, RICHARD L.

DENTAL FLOSS ROLL COMPRISING INTERCONNECTED PIECES EACH HAVING A PICK END

U.S. Pat. No. 3,744,499

In accordance with the invention claimed, a roll and method of packaging dental floss are disclosed and claimed which comprises a continuous piece of floss which is thickened, reinforced or rigid periodically along its length to form pick ends. The floss between adjacent pick ends forms a contiguous piece with the pick ends so that if the floss was severed adjacent a common end of each piece the floss remaining attached thereto and the pick end would result in a usable tool for penetrating and flossing the teeth.

CHARATAN, NORMAN

ORAL HYGIENE DEVICE

U.S. Pat. No. 4,836,227

An oral hygiene device comprised of a hollow housing having a weakened section in the periphery of the housing so that when the weakened section is broken, a user may grasp and separate the housing into two portions. A length of stretchable dental material and dentifrice is totally encased within a cavity in the unbroken housing and is secured at each end to two interior regions of the housing that can be separated at the weakened section.

CHARATAN, NORMAN

ORAL HYGIENE DEVICE

U.S. Pat. No. 5,174,314

An oral hygiene device employs a hollow plastic tube sealed at both ends. At least one area along the length of the tube is weakened and has its diameter in the weakened area reduced, but not reduced to zero diameter. A length of fiber, such as conventional dental floss, is stored within the length of the tube comprising the housing and has each of the free ends secured to a bulk of rigid material whose size does not permit the fibrous material from being able to escape the narrow diameter area.

EDISON, ROBERT G.

TOOTHPICK AND CONTAINER ASSEMBLY

U.S. Pat. No. 4,040,433

There is disclosed herein a reusable toothpick and container assembly. The assembly includes a toothpick having an elongated blade terminating at one end in a tip for removing debris from between the user's teeth and having at the other end a cap by which the toothpick can be grasped. The container is an elongated vial for holding mouthwash, into which the blade can be inserted and which can be sealed by the end cap. This provides for storage and cleansing of the toothpick between uses.

Consequently, as a review of the prior art indicates, a need exists for improvements in the construction of toothpick devices which will overcome the weaknesses of the prior art by providing a toothpick having an amount of dental floss contained therein which is easily accessible and usable by a human.

SUMMARY OF THE PRESENT INVENTION

The toothpick apparatus of the present invention consists of an elongated cylindrical device made of rolled wood having a thicker middle portion tapering away from the middle toward opposing ends or points. The toothpick has a perforated area or break point near its middle whereby when the toothpick is broken a useable length of dental floss is exposed. The dental floss is contained within layers of thin wood which are rolled in order to form the toothpick. Additional embodiments of the present invention are also described.

A primary object of the present invention is to provide a toothpick that will overcome the shortcomings of the prior art.

Another object of the present invention is to provide a toothpick which has a chamber within the frame of the toothpick.

Yet another object of the present invention is to provide an amount of dental floss located within the chamber of the toothpick.

Still yet another object of the present invention is to provide a perforation located at the center and along the circumference of the toothpick.

Yet another object of the present invention is to provide a toothpick which has an amount of dental floss and is easy to use.

Additional objects of the present invention will appear as the description proceeds.

The present invention overcomes the shortcomings of the prior art by providing a toothpick formed of rolled wood or like material wherein is located an amount of dental floss which is easily useable and accessible by the user.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

DESCRIPTION OF THE REFERENCE NUMERALS

Turning now descriptively to the drawings, in which similar reference characters denote similar elements throughout the similar views. The following numbering is used throughout the various drawings.

11 set of teeth
13 toothpick
15 two teeth
17 weakened area
19 tip of toothpick
21 layer of toothpick
23 dental floss
25 point of connection of floss and toothpick
27 piece of wood
29 corner of piece of wood
31 diagonally opposite corner of wood
33 cavity in wood
35 chamber in toothpick

DETAILS DESCRIPTION OF THE PREFERRED EMBODIMENT(S)

Figure 1:
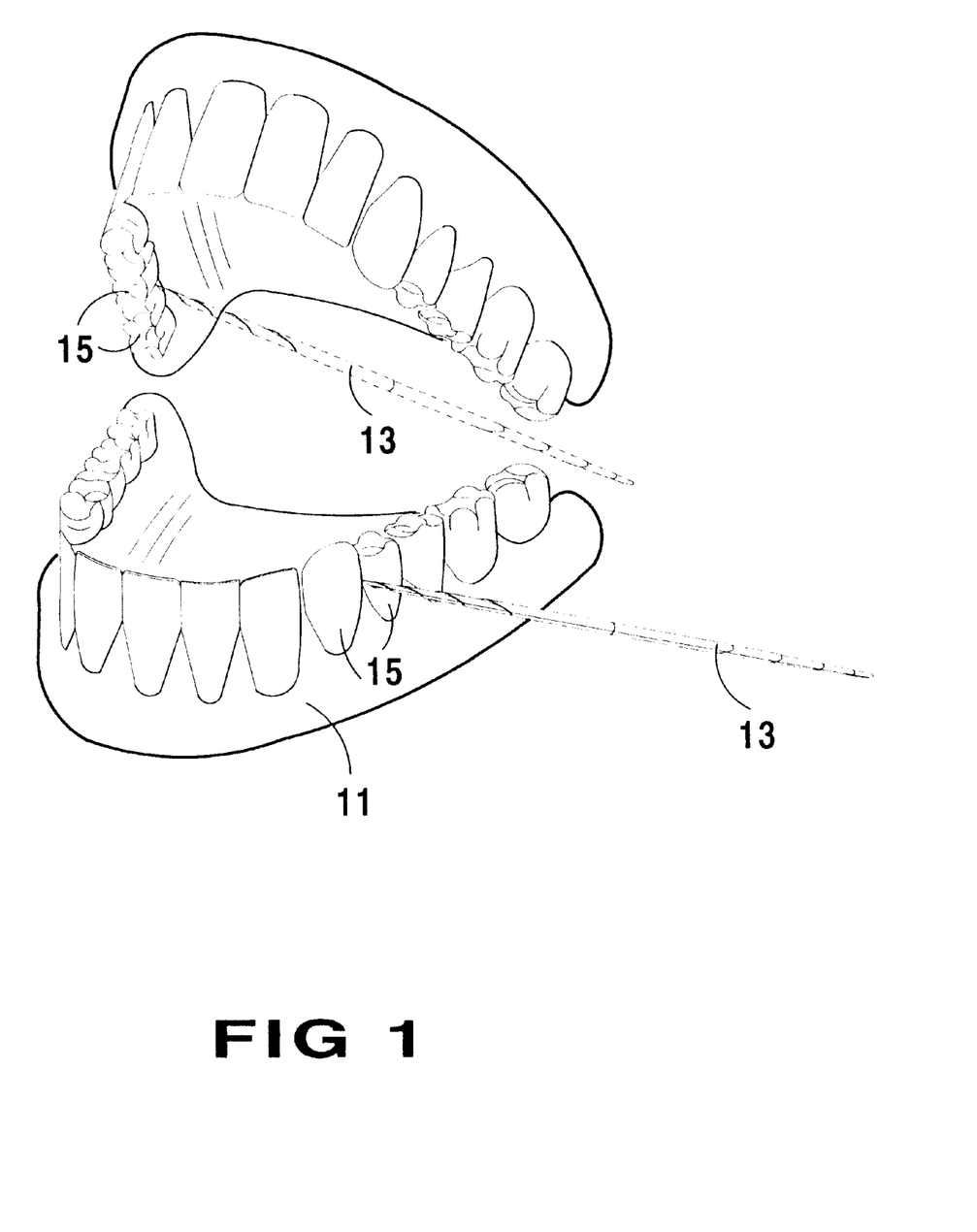
FIG. 1 is a perspective view of one embodiment of the present invention shown in operative connection with a set of teeth.

Turning to FIG. 1 therein is shown a perspective view of a set of human teeth, 11, wherein a toothpick, 13, according to the present invention is positioned on the outside surface and between a lower set of two teeth, 15, may be used to dislodge food particles from between said teeth, 15. Shown in outline is another toothpick, 13, wherein an unsuccessful attempt is made to dislodge food particles from the inside surface between an upper set of two teeth, 15. Because of the curved surface of the teeth illustrated by the upper set of teeth, 15, as they approach the gum line, the ideal position for the toothpick, 13, is to place an end on or near the gum line, pointed toward the top of the teeth and to move the toothpick away from the gum lime thereby dislodging and raising the food particles. As shown by the toothpick, 13, in outline the curved surface of the teeth, 15, would have a tendency to force the toothpick, 13, into the gum thereby causing damage to the gum area. An easy remedy for this type problem would be to use dental floss to clean the teeth in these difficult areas.

Figure 2:
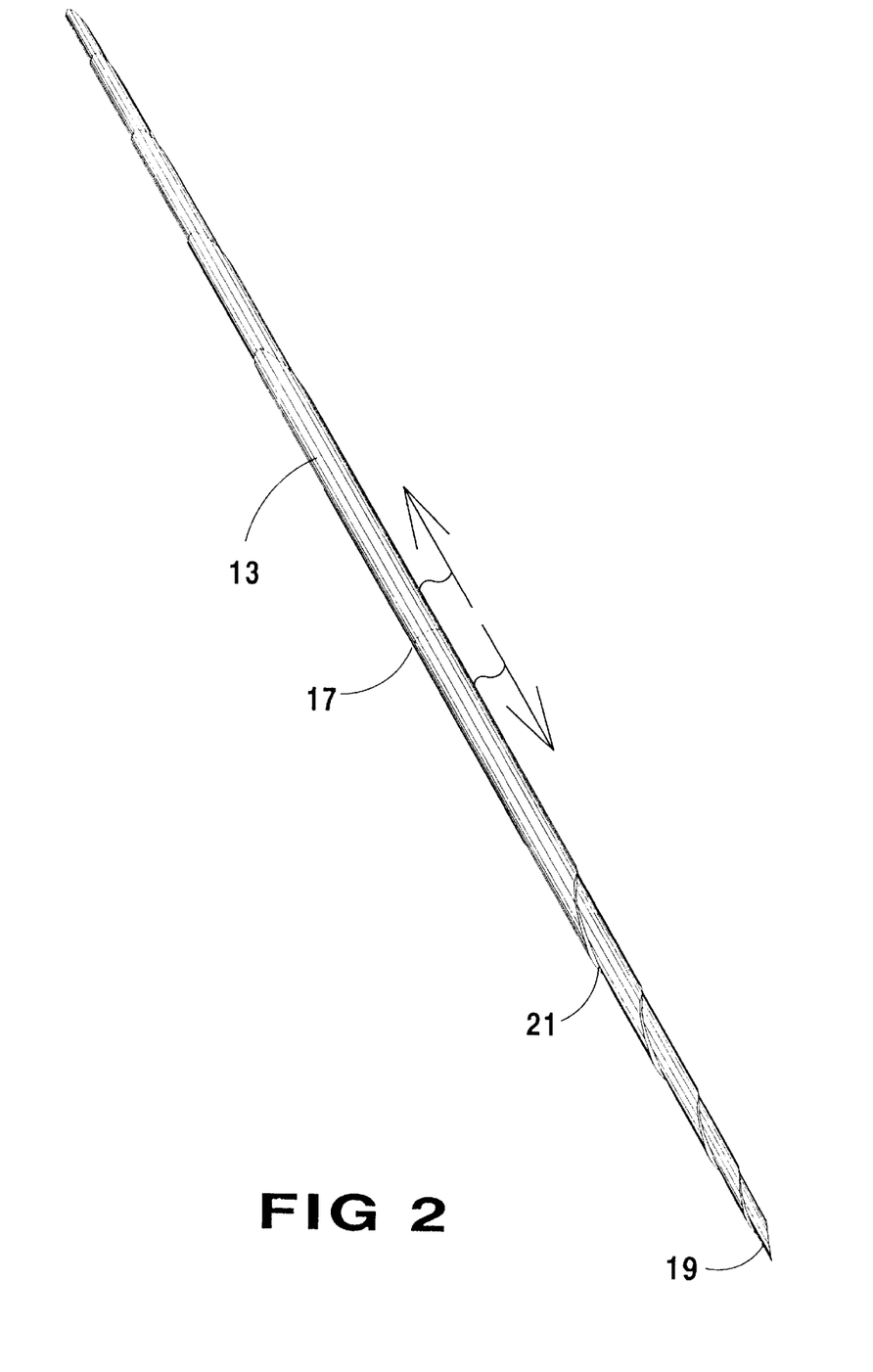
FIG. 2 is a perspective view of one embodiment of the present invention.

Turning to FIG. 2 therein is shown an enlarged view of the preferred embodiment of the present invention. Shown is the elongated cylindrical body of the toothpick, 13, having a perforation, break point, or weakened area, 17, located near the midpoint of the toothpick and extending around the circumference of the toothpick, 13, the toothpick being sized for use by humans.

Also shown is the thicker, middle portion, 17, of the toothpick, 13, which tapers away from the middle toward each end to a point, 19, or tip. Furthermore, therein are shown the continuous layers, 21, of effectively thin wood or like material for forming the toothpick, 13, with the layers, 21, being rolled or wrapped around and upon each other to form the toothpick, 13, so that the dental floss, 23, is interposed between the layers of wood, 21.

Figure 3:
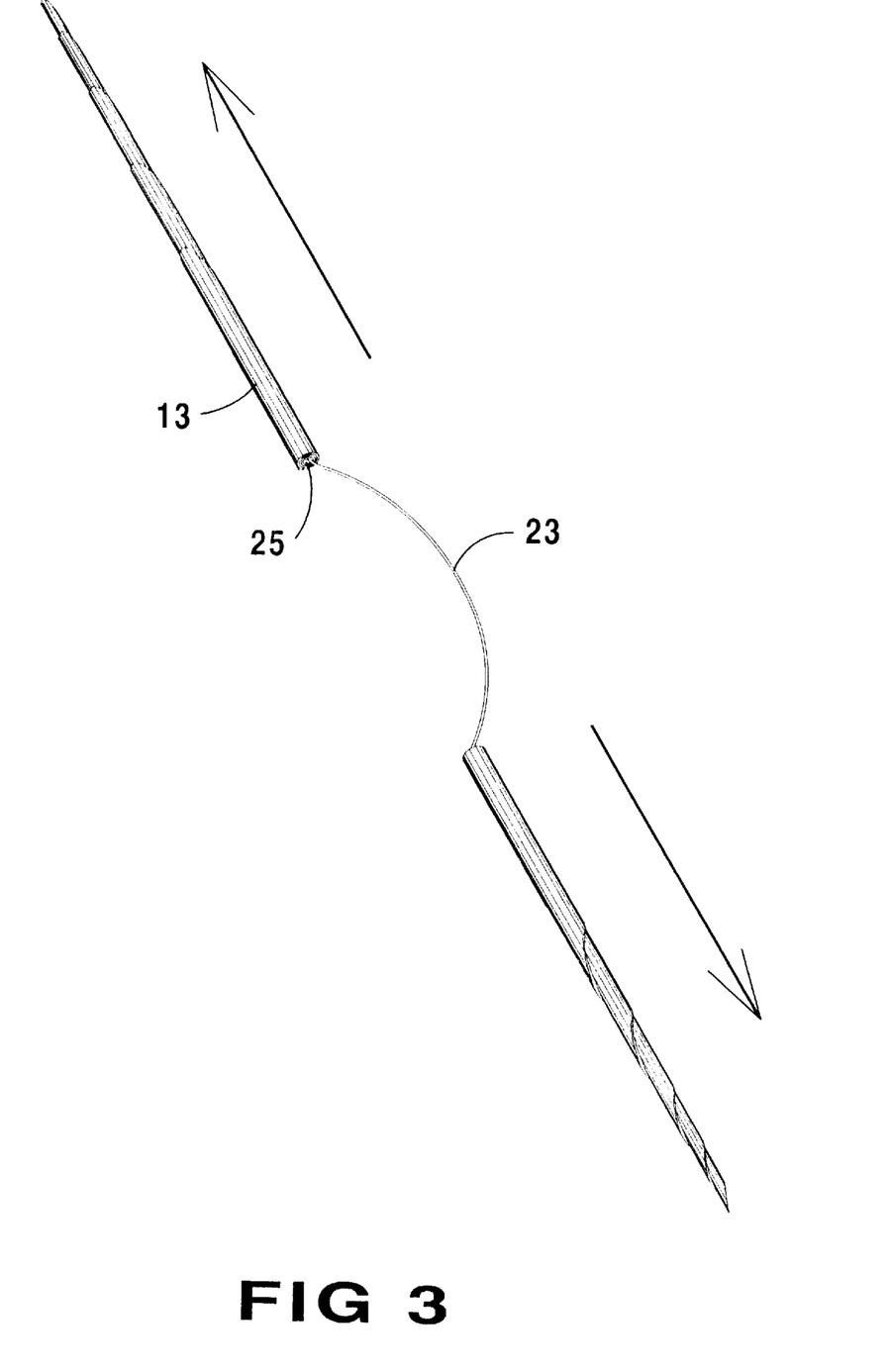
FIG. 3 is a perspective view of one embodiment of the present invention broken in half to expose the dental floss.

Turning to FIG. 3 therein is shown an enlarged view of the preferred embodiment of the present invention. Shown is the dental floss, 23, of the standard type, form and length suitable for human use which has been exposed and is accessible after the toothpick, 13, has been broken and the two pieces of the toothpick separated from each other.

The arrows of FIG. 3 merely indicate that the two ends, 19, of the toothpick, 13, are separated and disposed away from each other. The ends, 19, of the toothpick, 13, are separated by the user grasping opposing ends of the toothpick, 13, with opposite hands and physically breaking and separating the toothpick, 13, into the two pieces thereby exposing the dental floss, 23, which is shown still connected at 25 to each end of the toothpick, 13.

Figure 4:
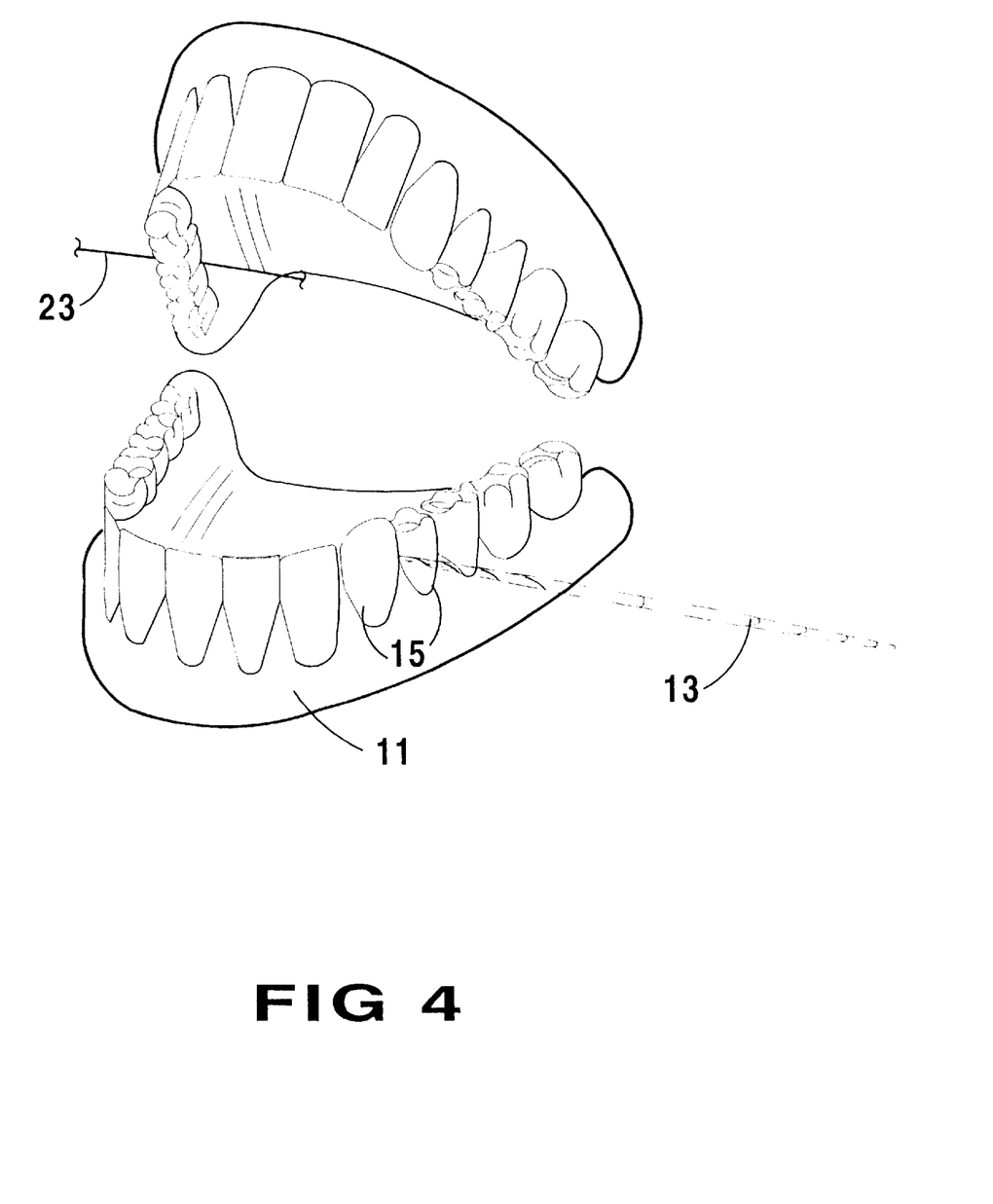
FIG. 4 is a perspective view of one embodiment of the present invention along with the dental floss shown in operative connection with a set of teeth.

Turning to FIG. 4 therein is shown a perspective view of a set of human teeth, 11, where a toothpick, 13, shown in outline, is positioned on the outside surface and between two lower teeth, 15, where it can be used to dislodge food particles from between the teeth, 15. After all accessible surfaces have been cleaned the toothpick, 13, can be broken and the dental floss, 23, removed and used to clean all remaining areas by passing it between and around all of the teeth.

Figure 5:
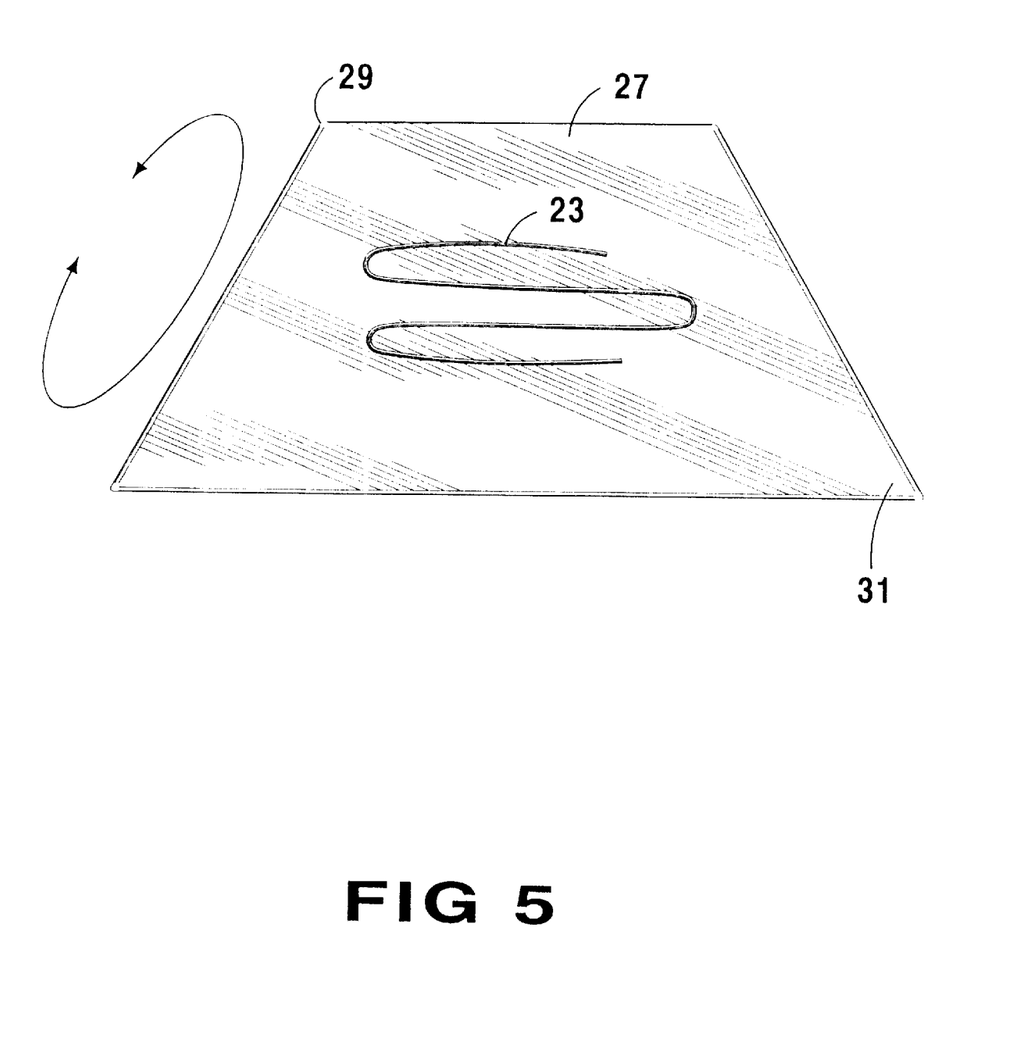
FIG. 5 is a perspective view of the preferred embodiment of the present invention showing dental floss placed on a piece of wood for forming the present invention.

Turning to FIG. 5 therein is shown a perspective view of the preferred embodiment of the present invention where a piece of dental floss, 23, is placed on a thin piece of wood, 27, or like material and the wood is rolled starting from one corner, 29, of the wood, 27, and continuing to the diagonally opposite corner, 31, and sealed by any means known within the art.

Rolling the thin wood, 27, forms the layers, 21, of the toothpick, 13, which were previously discussed above at FIG. 2. The floss, 23, becomes encased in and firmly held between the layers of wood as the wood, 27, is rolled over and upon itself. Thereafter, when the toothpick, 13, is broken apart into two pieces, the floss, 23, remains connected to the toothpick, 13, at 25 until the floss is removed by the user.

Figure 6:
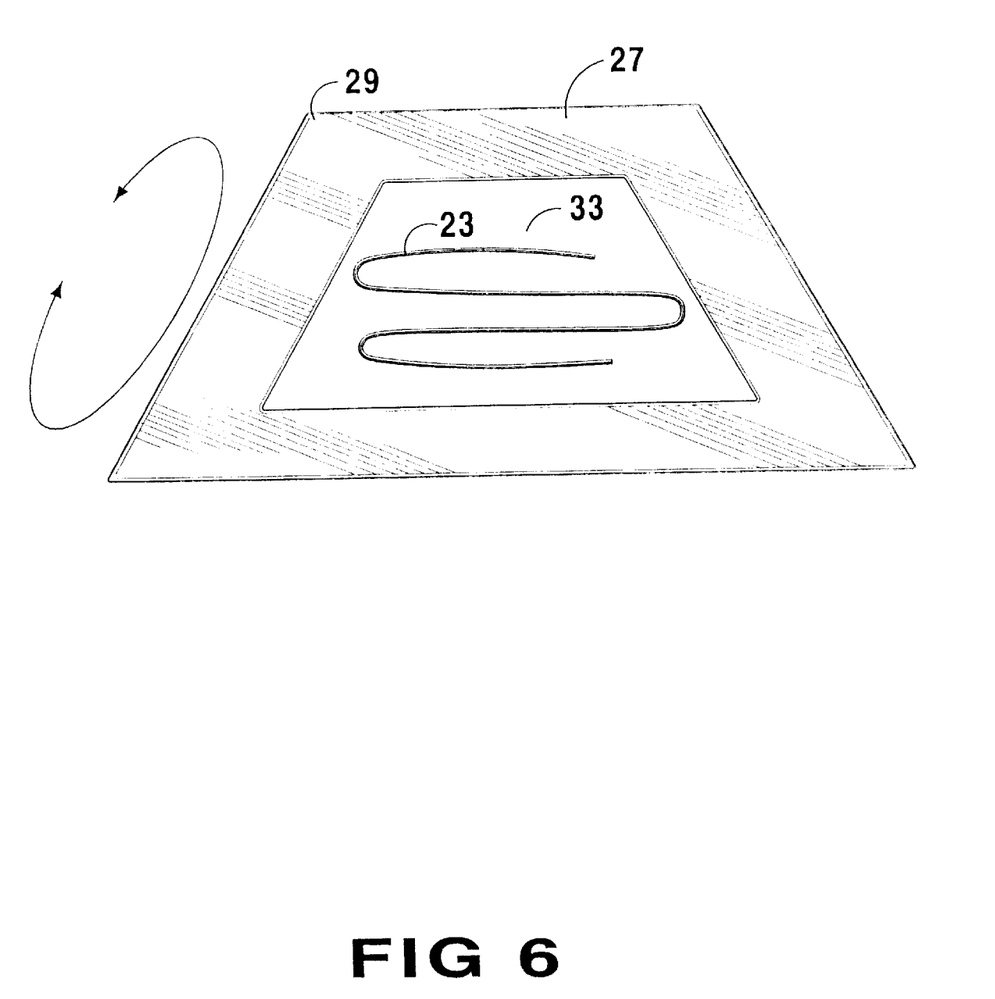
FIG. 6 is a perspective view of one embodiment of the present invention showing a cavity in a piece of wood with dental floss for forming the present invention.

Turning to FIG. 6 therein is shown a perspective view of an alternate embodiment of the present invention wherein a cavity, 33, is formed within the piece of wood, 27, due to the elimination of the wood, wherein the dental floss, 23, is placed and the wood is rolled starting from one corner, 29, and continuing to the diagonally opposite corner.

Regarding the embodiment of FIG. 6, when the toothpick, 13, is broken into two pieces, the floss, 23, will more likely fall freely from the cavity, 33, the toothpick, 13, and will not remain connected to the toothpick at what has previously been identified in FIG. 6 as 25.

Figure 7:
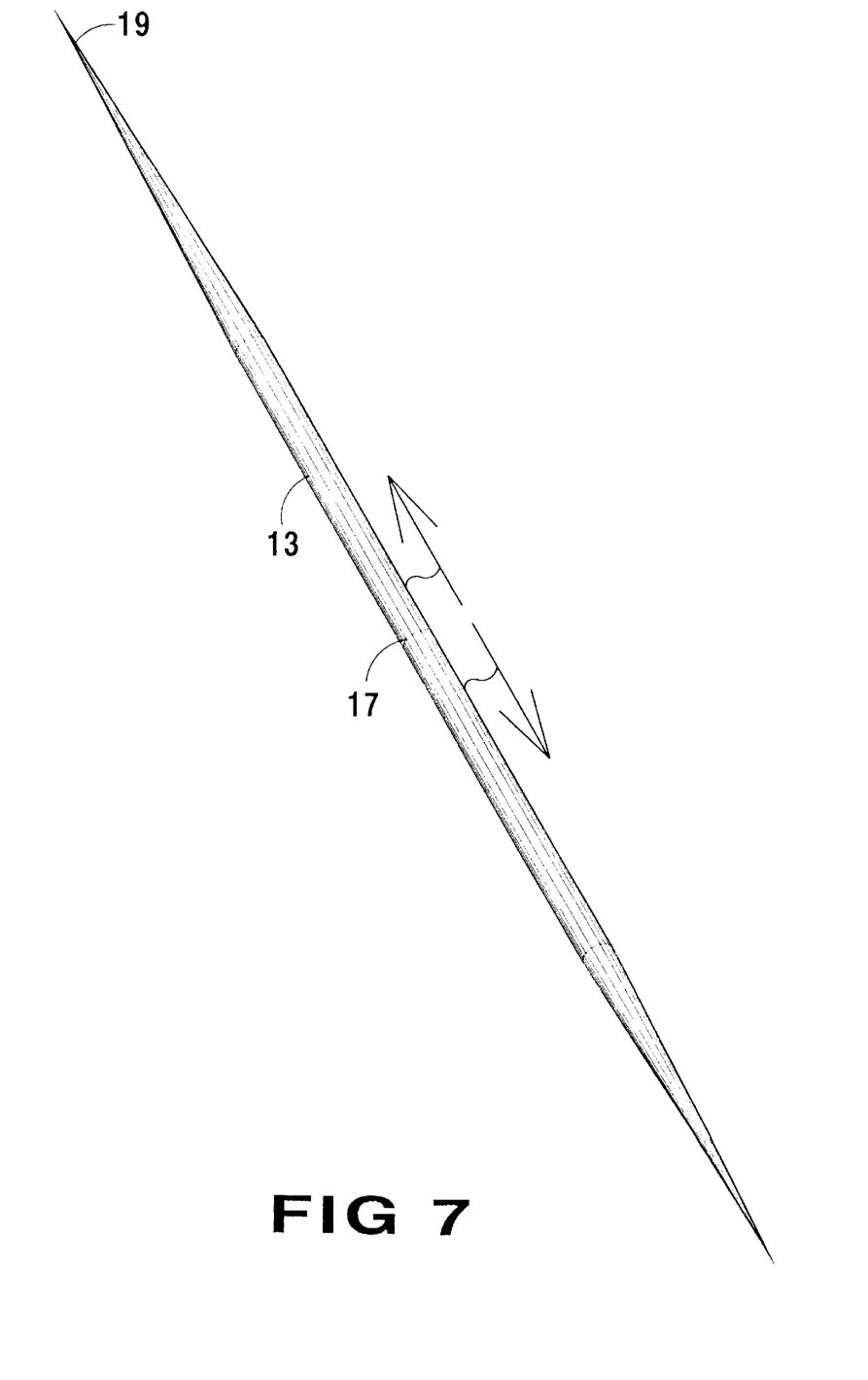
FIG. 7 is a perspective view of one embodiment of the present invention showing the body of the present invention adapted for having a chamber therein for holding dental floss.

Turning to FIG. 7 therein is shown a perspective view of another embodiment of the present invention whereby a two piece toothpick, 13, is formed from plastic or like material having a chamber (not shown) located within to hold an amount of dental floss (not shown) suitable for human use.

Figure 8:
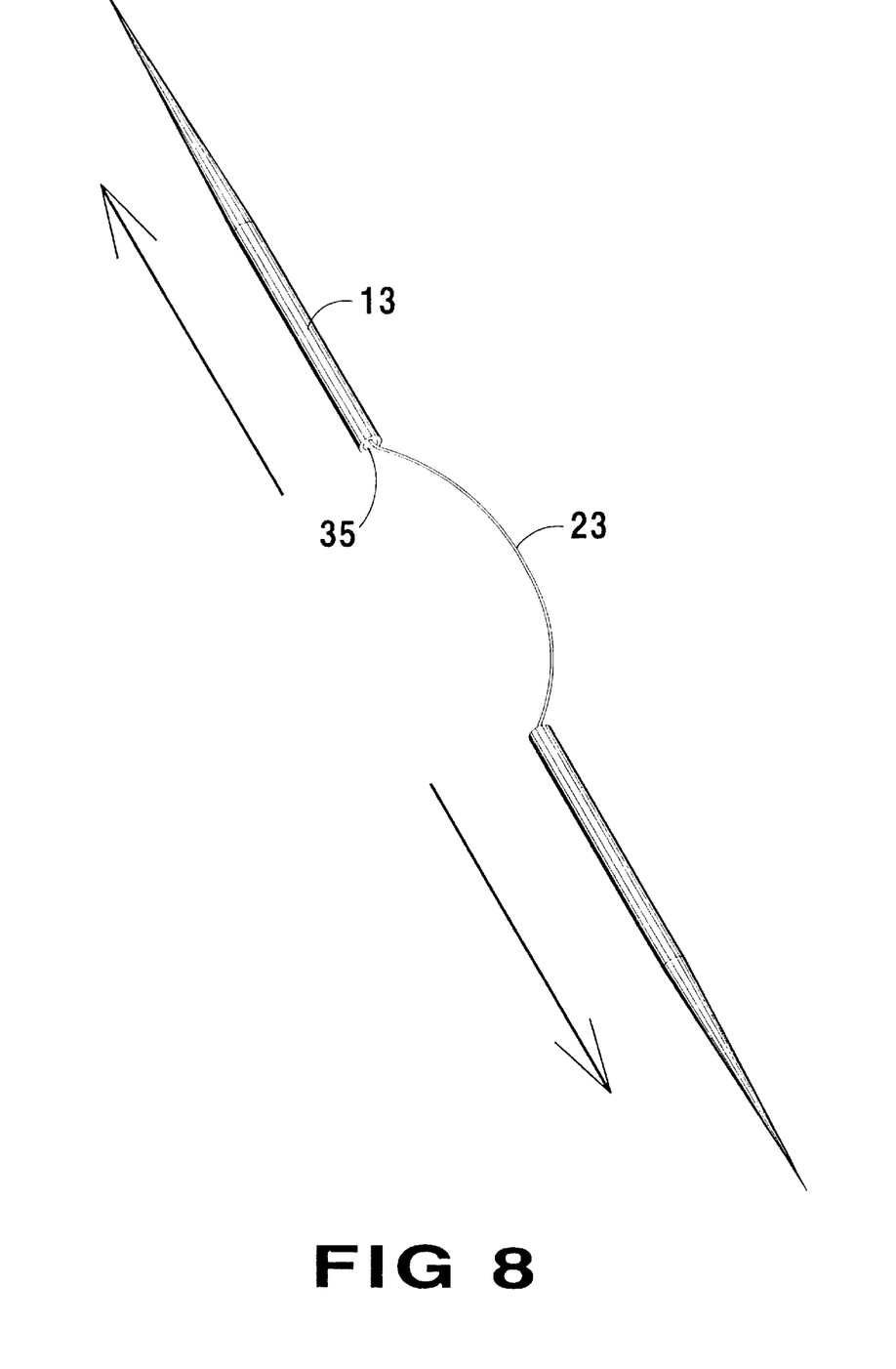
FIG. 8 is a perspective view of one embodiment of the present invention showing the body having a chamber therein for holding dental floss.

Shown is the toothpick, 13, having a perforation, break point, or weakened area, 17, located near the midpoint of the toothpick and extending around the circumference of the toothpick, 13. Also shown is the thicker, middle portion, 17, of the toothpick, 13 which tapers away from the middle toward each end to a tip or point, 19. FIG. 8 is an enlarged view of the other embodiment of the present invention shown in FIG. 7. Shown is the dental floss, 23, which has been exposed and is accessible after the toothpick, 13, has been broken and the two pieces of the toothpick separated from each other.

Shown also is the chamber, 35, formed in the toothpick, 13, to hold an amount of dental floss, 23 suitable for use by humans.

What is claimed as new and desired to be protected by letters patent is set forth in the appended claims:

1. A method of forming an apparatus for cleaning teeth, comprising the steps of:
    a) forming an elongated cylindrical body sized for use by humans being thicker in the middle and tapering from the middle to opposing tips;
    b) forming said body by rolling an effectively thin layer of wood; and,
    c) interposing dental floss between said layers of effectively thin wood whereby said dental floss is removable for use by humans, and further comprising the step of forming a cavity within said body due to the elimiantion of said wood, whereby said cavity contains said dental floss for use by humans.

* * * * *